United States Patent
Maruyama

(10) Patent No.: US 8,486,999 B2
(45) Date of Patent: Jul. 16, 2013

(54) LONG-CHAIN OXYAMINOPOLYOL BASED GELATOR AND GEL

(75) Inventor: Tatsuo Maruyama, Kobe (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 417 days.

(21) Appl. No.: 12/693,009

(22) Filed: Jan. 25, 2010

(65) Prior Publication Data

US 2011/0034552 A1 Feb. 10, 2011

(30) Foreign Application Priority Data

Aug. 6, 2009 (JP) ................................. 2009-183882

(51) Int. Cl.
*A61K 31/00* (2006.01)

(52) U.S. Cl.
USPC ........................................... 514/538; 560/37

(58) Field of Classification Search
USPC ........................................... 514/538; 560/37
See application file for complete search history.

(56) References Cited

U.S. PATENT DOCUMENTS 5,624,906 A * 4/1997 Vermeer ........................ 514/23

FOREIGN PATENT DOCUMENTS

| JP | A-2002-85957 | 3/2002 |
| JP | A-2003-327949 | 11/2003 |
| JP | A-2004-250797 | 9/2004 |

OTHER PUBLICATIONS

Petka et al., "Reversible Hydrogels from Self-Assembling Artificial Proteins," *Science*, Jul. 17, 1998, pp. 389-392, vol. 281.

Aggeli et al., "Self-Assembling Peptide Polyelectrolyte β-Sheet Complexes Form Nematic Hydrogels," *Angewandte Chemie*, 2003, pp. 5603-5606, vol. 42.

Hartgerink et al., "Self-Assembly and Mineralization of Peptide-Amphiphile Nanofibers," *Science*, Nov. 23, 2001, pp. 1684-1688, vol. 294.

Matsumoto et al., "The Supramolecular Hydrogel toward The Smart Biomaterials," *Dojin News*, 2006, pp. 1-16, No. 11 (with Abstract).

(Continued)

*Primary Examiner* — Deborah D Carr
(74) *Attorney, Agent, or Firm* — Oliff & Berridge, PLC

(57) ABSTRACT

[PROBLEMS TO BE SOLVED]
It is an object of the present invention to provide a gelator containing a long chain oxyaminopolyol capable of forming a gel with a small amount thereof over a liquid property range from acidic to alkaline, and a gel having high environmental suitability, biocompatibility and biodegradability.

[MEANS FOR SOLVING THE PROBLEMS]
A gelator, characterized by containing a long chain oxyaminopolyol of Formula (I):

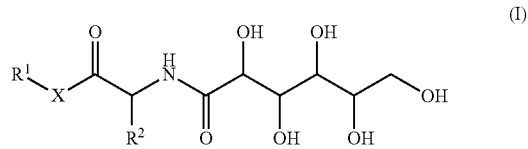

(where $R^1$ is a $C_{12-16}$ saturated aliphatic group or a $C_{12-16}$ unsaturated aliphatic group having one double bond; $R^2$ is a substituent which an amino acid has; and X is an oxygen atom or NH)
and a pharmaceutically acceptable salt thereof; a self-assembly formed by the self-assembly of the gelator; and a gel containing the gelator or the self-assembly, and water, an aqueous solution, a hydrophilic organic solvent or a hydrophilic organic solution, or a hydrophobic organic solvent or a hydrophobic organic solution.

6 Claims, 1 Drawing Sheet

(a)  (b)  (c)  (d)

OTHER PUBLICATIONS

Yang et al., "Conjugate of naphthalene and dipeptides produce molecular hyrdogelators with high efficiency of hydrogelation and superhelical nanofibers," *Journal of Materials Chemistry*, 2007, pp. 850-854, vol. 17.

Suzuki et al., "Supramolecular hydrogel formed by glucoheptonamide of L-lysine: simple preparation and excellent hydrogelation ability," *Tetrahedron*, 2007, pp. 7302-7308, vol. 63.

* cited by examiner

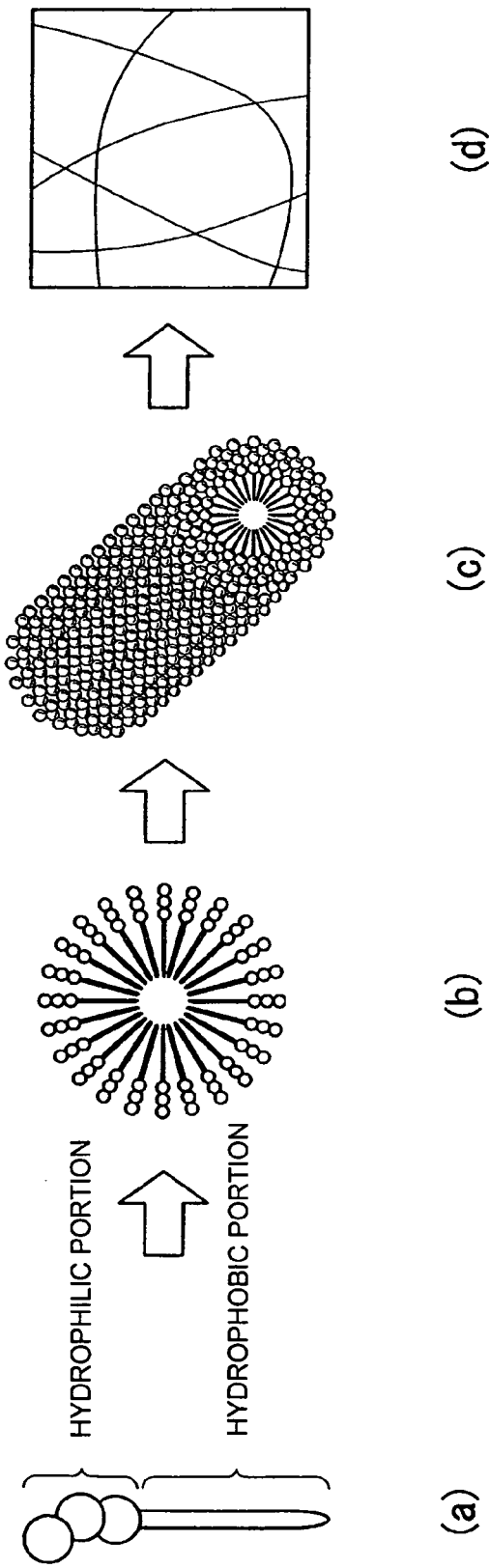

LONG-CHAIN OXYAMINOPOLYOL BASED GELATOR AND GEL

TECHNICAL FIELD

The present invention relates to a novel long chain oxyaminopolyol-based gelator that is easily produced in an industrial scale, a self-assembly formed by self-assembly of the gelator, and a gel composed of the gelator or the self-assembly and various aqueous solutions.

The long chain oxyaminopolyol-based gelator of the present invention is a gelator capable of being easily synthesized by two times of a reflux reaction and can be suitably utilized in the production of various gel form base materials, for example, cosmetic sundry goods such as cosmetics, breath deodorizer products and contact lens care products; perfume products; gel form foods such as agar; and pharmaceutical preparations. In addition, a gel obtained from the gelator is suitably utilized as various functional materials, for example, cosmetic sundry goods such as cosmetics, breath deodorizer products and contact lens care products; perfume products; commodity applications such as (soft) contact lenses, paper diapers and aromatics; dry-land agricultural applications; chemical analysis applications such as chromatography; medicine and pharmacy applications; and biochemistry field applications such as carriers of protein, cell culture-related base materials, and a bioreactor.

BACKGROUND ART

A hydrogel contains water as the medium, so that it is useful as a gel having high biocompatibility and is used in various fields such as applications for commodities such as paper diapers, cosmetics and aromatics.

Examples of a related-art hydrogel include natural polymer gels such as agarose, and synthetic polymer gels in which between polymer chains is crosslinked through a chemical covalent bond, such as an acrylamide gel.

Recently, functional gels in which various functions such as material retention capacities, an external stimulus responsive performance and a biodegradability in consideration of the environment are imparted to a hydrogel, are attracting attention, and there are performed attempts for developing various functions by introducing functional molecules into the natural or the synthetic polymer gels using a copolymerization reaction or the like.

Thus, for imparting new functions to a hydrogel, studying the nanostructure and the surface structure of the gel in detail is required. However, the above method for introducing functional molecules using a copolymerization reaction has various problems such as problems in which the introduction rate of functional groups is limited and a precise molecule design is difficult, a safety problem of unreacted remaining materials, and further a problem in which the preparation of the gel is extremely cumbersome.

As opposed to such a related-art "top-down type" development of functional materials, there is attracting attention a "bottom-up type" study for creating functional materials by which atoms or molecules which are the minimum units of substances are assembled, and in the resultant assembly which is a supramolecule, new functions are discovered.

Also in the field of the gel, the development of a novel gel formed from a non-covalent gel fiber (so-called "nanofiber-shaped self-assembly") produced by the self-assembly of a low molecular weight compound has been progressing. This "self-assembly" indicates such a phenomenon that in a substances (molecules) group in a random state at first, molecules associate spontaneously by an intermolecular non-covalent interaction or the like under an appropriate external condition to grow to a macro functional assembly.

The novel gel attracts attention in such a point that the control of the macroscopic structure or function of the gel is theoretically possible by controlling an intermolecular interaction or a weak non-covalent bond of a molecule assembly according to a molecule design of a monomer.

However, with respect to the way of controlling the intermolecular interaction or non-covalent bond between low molecular weight compounds, there is not yet found an apparent methodology. In addition, in the study of the non-covalent gel, because of relative easiness of the gel formation, the study of a self-assembly utilizing a hydrogen bond in an organic solvent is preceded but the study of a self-assembled compound (that is, such as a hydrogelator) in an aqueous solution remains in accidental findings.

Hydrogelators for forming a non-covalent gel which have been reported until now are broadly divided into the following three categories.

[1. Hydrogelators Having an Amphipathic Low Molecular Weight Molecule as the Skeleton Thereof]

This type of hydrogelators is created with an artificial lipid film as a model, and examples of the hydrogelators include surfactant-type gelators having a quaternary ammonium salt portion as a hydrophilic portion and having an alkyl long chain as a hydrophobic portion, and ampholytic surfactant-type gelators in which hydrophilic portions of two surfactant-type molecules are coupled.

As one example of the hydrogel formed by such gelators, there is disclosed a molecule organizational hydrogel formed by adding an anion having a molecular mass of 90 or more to a dispersion aqueous solution of a cationic amphipathic compound having a branched alkyl group in the hydrophobic portion (Patent Document 1).

[2. Hydrogelators Having a Skeleton in the Motif of Intravital Components]

Examples of this type of hydrogelators include gelators utilizing an association between molecule-assemblies through a peptide secondary structure skeleton (such as α-helix structure and β-sheet structure).

For example, there are disclosed a gelator having an α-helix structure (Non-patent Document 1) and a gelator having a β-sheet structure (Non-patent Document 2).

[3. Hydrogelators Having a Semi-Artificial Low Molecular Weight Molecule as the Skeleton Thereof]

This type of hydrogelators is composed of a combination of intravital components (hydrophilic portion), such as DNA bases, peptide chains, and sugar chains, and alkyl chains (hydrophobic portion) and the like, and can be called as a gelator combining characteristics of the above two types of gelators. Here, the DNA base, the peptide chain, and the sugar chain assume not only a role of enhancing the hydrophilicity, but also a role of imparting an intermolecular interaction such as a hydrogen bond.

For example, there are disclosed a hydrogelator containing a glycoside amino acid derivative having a sugar structure moiety having a glycoside structure of an N-acetylated monosaccharide or disaccharide (Patent Document 2), and disclosed a fine hollow fiber formed by the self-assembly from a peptide lipid of General Formula: $RCO(NHCH_2CO)_mOH$ and a transition metal (Patent Document 3).

In addition, it is disclosed that an amphipathic peptide having a structure of (hydrophobic portion-cysteine residue (forming a disulfide bond during the network formation)-glycine residue (imparting flexibility)-phosphorylated serine residue-cell adhesive peptide) forms a β-sheet type fiber network with a nuclear of the hydrophobic portion (Non-patent Document 3).

In addition, there is also disclosed a case where a sugar lipid-type supramolecule hydrogel was produced using a chemical library (Non-patent Document 4).

An amphipathic dipeptide compound composed of a hydrophobic portion and a dipeptide attracts attention as one of "bottom up-type" functional materials capable of forming a self-assembly. Examples of the dipeptide compound include dipeptide compounds having a special lipid portion such as "2-(naphthalene-2-yl-oxy)acetic acid"+"glycylglycine, glycylserine or the like" which are known to become a hydrogel. However, any of these dipeptide compounds gels is produced by gelling an acidic aqueous solution, or a hydrogel produced by the gelation of any of these dipeptide compounds is acidic (Non-patent Document 5).

On the contrary, a lipid peptide compound composed of lauric acid or myristic acid which is a natural aliphatic acid and glycylglycine does not become a hydrogel and forms an organic nanotube having a hollow of multiple vesicles having an inner diameter of around 50 to 90 nm to be deposited (for example, Patent Document 3).

In addition, a lipidaminopolyol among amphipathic compounds is used as a surfactant or an emulsifier (Non-patent Document 6), however, a self-assembly formed by the self-assembly of a lipidaminopolyol (1a to 3a) described in the same document cannot form a hydrogel.

RELATED-ART DOCUMENTS

Patent Documents

[Patent Document 1]
Japanese Patent Application Publication No. JP-A-2002-85957
[Patent Document 2]
Japanese Patent Application Publication No. JP-A-2003-327949
[Patent Document 3]
Japanese Patent Application Publication No. JP-A-2004-250797

Non-Patent Documents

[Non-Patent Document 1]
W. A. Pekata et al., SCIENCE, vol. 281, p. 389 (1998)
[Non-Patent Document 2]
A. Aggeli et al., Angew. Chem. Int. Ed., vol. 42, pp. 5603 to 5606 (2003)
[Non-Patent Document 3]
Jefffry D. Hartgerink, Elia Beniaah, Samuel I. Stupp, SCIENCE, vol. 294, pp. 1684 to 1688 (2001)
[Non-Patent Document 4]
Shinji Matsumoto, Itaru Hamachi, Dojin News, No. 118, pp. 1 to 16 (2006)
[Non-Patent Document 5]
Z. Yang, B. Xu et al., J. Mater. Chem., vol. 17, pp. 850 to 854 (2007)
[Non-Patent Document 6]
M. Suzuki, S. Owa, H. Shirai and K. Hanabusa, Tetrahedron, vol. 63, pp. 7302 to 7308 (2007)

SUMMARY OF THE INVENTION

Problems to be Solved by the Invention

In a related-art hydrogel, for forming a synthetic polymer gel of the hydrogel, or depending on the case, for gelling a natural polymer such as a gelatin (collagen), a crosslinker having an aldehyde group is necessary to be used.

In addition, for imparting functions to a (synthetic) polymer gel, needless to say to a natural polymer gel, a copolymerization reaction is necessary to be effected for chemically modifying a polymer chain or for introducing a functional molecule.

Thus, a related-art hydrogel has such problems that the preparation of the gel is cumbersome and that an unreacted crosslinker or unreacted substances during the copolymerization reaction remain(s) in the hydrogel.

In addition, in the case (1.) where the above described hydrogelators for forming a non-covalent gel which have been disclosed hitherto, have the amphipathic low molecular weight molecule as the skeleton, the gel formation may not be achieved, depending on the liquid property of the medium. In other words, in an alkaline range, a reaction mixture forms a micelle to become an emulsified liquid. On the other hand, although in an acidic range, the low molecular weight molecules are self-assembled in a fiber shape and a hydrogel can be obtained, there is disclosed substantially no example in which the hydrogelation is achieved in a neutral range regarded as safe for the organism. In addition, the related-art hydrogel also has a problem that there is still a concern about the safety of a quaternary ammonium cation (for example, Patent Document 1) and the like for the organism environment.

In addition, in the case (2.) where the hydrogelators have a skeleton in the motif of intravital components, the hydrogelators have such a problem concerning the productivity that they are not suitable for the mass production and a problem that the gel forming ability depends on temperature and pH.

Further, in the case (3.) where the hydrogelators have a semi-artificial low molecular weight molecule as the skeleton, for example, referring to a reaction scheme (FIG. 1) for synthesizing a glycoside amino acid derivative constituting the hydrogelator described in Patent Document 2, there is specified that sodium azide having high toxicity is used, or for self-assembling a hollow fiber described in Patent Document 3, it is essential to add a transition metal (ion). Because of this, these examples leave a problem concerning biocompatibility and the environmental safety.

Thus, various non-covalent hydrogels and hydrogelators for forming the gels which have been hitherto disclosed are those for which further improvements are required in terms of the gel forming ability (gel structure retaining ability), the safety for the organism environment and the like.

Further, from the viewpoint of the safety for the organism environment, there is a potential requirement for a hydrogelator capable of forming a gel with a smaller adding amount.

In order to solve the problems described above, it is an object of the present invention to provide a gelator produced using a higher alcohol, a natural amino acid and a polyol which have safety and high general versatility as used in cosmetics and pharmaceutical preparations, capable of being industrialized because the gelator can be inexpensively and easily obtained by a two-staged reaction of two types of reflux reactions, and containing a lipidaminopolyol having high gelling ability to form a gel even with a small amount of the gelator.

Particularly, it is an object of the present invention to provide a gelator having high gelling ability capable of forming a gel by adding an extremely small amount of the gelator to an aqueous solution in which an alcohol or an organic solvent is mixed or an aqueous solution in which an inorganic salt or an organic salt is dissolved, over a wide range of liquid properties ranging from acidic to alkaline, particularly even in a neutral range.

It is another object of the present invention to provide a gel retaining a gel structure stably over a wide range of liquid properties ranging from acidic to alkaline, and having high environmental suitability, biocompatibility and biodegradability.

Means for Solving the Problems

The present invention relates to, according to a first aspect, a gelator characterized by containing a long chain oxyaminopolyol of Formula (I):

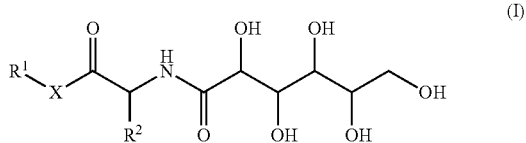

(where $R^1$ is a $C_{12-16}$ saturated aliphatic group or a $C_{12-16}$ unsaturated aliphatic group having one double bond; $R^2$ is a hydrogen atom, a $C_{1-4}$ alkyl group which optionally has a $C_{1-2}$ branched chain, a phenylmethyl group or a $—(CH_2)_n—Y$ group (where n is a number of 1 to 4; and Y is an amino group, a guanidino group, a $—CONH_2$ group or a fused heterocycle composed of a 5-membered ring, a 6-membered ring or a 5-membered ring and a 6-membered ring which optionally have 1 to 3 nitrogen atom(s)); and X is an oxygen atom or a NH group), or a pharmaceutically available salt of the long chain oxyaminopolyol.

According to a second aspect, the gelator according to the first aspect is characterized in that $R^2$ is a hydrogen atom, a methyl group, an isopropyl group, a sec-butyl group, an isobutyl group or a phenylmethyl group.

According to a third aspect, the gelator according to the first aspect is characterized in that $R^1$ is a $C_{14-16}$ saturated aliphatic group.

According to a fourth aspect, the gelator according to the third aspect is characterized in that $R^1$ is a palmityl group.

According to a fifth aspect, a self-assembly is formed by self-assembly of the gelator according to any one of the first aspect to the fourth aspect.

According to a sixth aspect, a gel contains the gelator according to any one of the first aspect to the fourth aspect or the self-assembly according to the fifth aspect, and water, an aqueous solution, a hydrophilic organic solvent, a hydrophilic organic solution, a hydrophobic organic solvent or a hydrophobic organic solution.

According to a seventh aspect, in the gel according to the sixth aspect, the hydrophilic organic solvent is at least one selected from a group consisting of methanol, ethanol, 2-propanol, isobutanol, pentanol, hexanol, 1-octanol, isooctanol, acetone, dioxane, glycerin, propylene glycol and ethylene glycol.

According to an eighth aspect, in the gel according to the sixth aspect, the hydrophilic organic solution is a solvent mixture of the hydrophilic organic solvent according to the seventh aspect and water.

According to a ninth aspect, in the gel according to the sixth aspect, the aqueous solution is an aqueous solution in which there is dissolved an organic acid, or an inorganic acid, or at least one of inorganic salt selected from a group consisting of an inorganic carbonate salt, an inorganic sulfate salt, an inorganic phosphate salt and an inorganic hydrogen phosphate salt, or at least one of organic salt selected from a group consisting of an inorganic acetate salt, an inorganic sulfate salt, an inorganic citrate salt, an organic amine hydrochloride salt and an organic amine acetate salt.

According to a tenth aspect, in the gel according to the ninth aspect, the organic acid is at least one of organic acid selected from a group consisting of acetic acid, citric acid, succinic acid, lactic acid, malic acid, maleic acid, fumaric acid and trifluoroacetic acid, the inorganic acid is at least one of inorganic acid selected from a group consisting of hydrochloric acid, phosphoric acid, carbonic acid, sulfuric acid, nitric acid and boric acid, the inorganic salt is at least one of inorganic salt selected from a group consisting of calcium carbonate, sodium carbonate, potassium carbonate, sodium sulfate, potassium sulfate, magnesium sulfate, potassium phosphate, sodium phosphate, disodium hydrogen phosphate and sodium dihydrogen phosphate, and the organic salt is at least one of organic salt selected from a group consisting of sodium acetate, potassium acetate, sodium lactate, potassium lactate, sodium citrate, potassium citrate, ethylenediamine hydrochloride salt, ethylenediamine tetraacetate salt and tris-hydroxymethylaminomethane hydrochloride salt.

According to an eleventh aspect, in the gel according to the sixth aspect, the hydrophobic organic solvent is at least one selected from a group consisting of a vegetable oil, an ester and a hydrocarbon.

According to a twelfth aspect, in the gel according to the sixth aspect, the hydrophobic organic solution is a solvent mixture of the hydrophobic organic solvent according to the eleventh aspect and water.

According to a thirteenth aspect, in the gel according to the sixth aspect, the aqueous solution is an aqueous solution selected from a group consisting of aqueous solutions of pH 2 to 8.

Effects of the Invention

The gelator of the present invention can form a gel by gelling an aqueous medium such as water, an aqueous solution, a hydrophilic organic solvent and a hydrophilic organic solution without using a crosslinker or the like required during the formation of a related-art gel, so that a problem of the remaining of an unreacted crosslinker is not caused. In addition, the gelator of the present invention contains low molecular weight compounds, so that it can form a gel without containing unreacted substances of functional molecules introduced into a related-art gelator for developing functions.

Moreover, the gelator of the present invention makes it possible to form the gel from not only the above described aqueous medium, but also a hydrophobic medium, for example, a hydrophobic organic solvent such as oils and a hydrophobic organic solution.

In addition, the gelator of the present invention differs from a related-art low molecular weight molecule-type gelator in such a term that the gelator of the present invention is composed of a higher alcohol, a polyol and a natural amino acid which can be used as an additive for cosmetics or medicines, so that the gelator has high safety for the organism. Moreover, the gelator of the present invention can be synthesized easily and in a large amount by two times of a reflux reaction, so that it is also an economically excellent low molecular weight molecule-type gelator.

Further, the gelator of the present invention can form a gel over a wide range of liquid properties ranging from acidic to alkaline also from a hydrophilic organic solvent, an aqueous solution in which a hydrophilic organic solvent is mixed, and an aqueous solution in which an inorganic acid, an organic acid, an inorganic salt or an organic salt is dissolved. Particularly, from the viewpoint of high safety required for a cell culture base material, medical materials, materials for cosmetics or the like, the gelator of the present invention having a gel forming ability relative to various aqueous solutions even in a neutral range is extremely useful in the above applications.

In addition, the gelator of the present invention can have a gel forming ability as a gelator, also when the gelator produced by mixing two or more types of long chain oxyaminopolyols constituting the gelator is used.

Further, even when the gelator of the present invention is produced by mixing, besides the long chain oxyaminopolyols of Formula (I), other various peptides capable of forming a self-assembly, that is, tripeptides or tetrapeptides modified with an aliphatic acid at the N terminal thereof, each of them or a combination of them can form a self-assembly.

In addition, the gelator of the present invention can form a self-assembly by mixing the gelator with a surfactant even in an aqueous solution in which an anionic surfactant, a nonionic surfactant or a cationic surfactant is dissolved.

In addition, by the gelator of the present invention, a low molecular weight compound is adsorbed to a self-assembly formed by the self-assembly or is included in the self-assembly, so that a gel capable of sustained-releasing the low molecular weight compound can be formed.

In addition, the gelator of the present invention is an artificial low molecular weight compound composed of only lipid and a peptide and using no animal-derived material (such as collagen, gelatin and matrigel) of which use is recently concerned due to a problem of BSE infection or the like, so that the gel obtained causes no problem of the infection or the like. Moreover, the gelator can be produced only by an amidation reaction of lipid and a peptide without using a reagent having a high reactivity but having toxicity, such as sodium azide, so that it can be preferably used as a gelator having high safety.

In addition, the gelator of the present invention can also be used for an application, as other than the gel, as a cell damage protecting material, a Langmuir monolayer, and the like.

In addition, with respect to the self-assembly of the present invention, when the gelator is self-assembled with a central focus on a hydrophobic group, a polyol portion becomes positioned in the outermost side (that is, the surface of the self-assembly), so that when the self-assembly is incorporated into an organism, the self-assembly is difficult to cause a rejection against organism cells and is excellent in cell-adhesiveness. Therefore, the self-assembly can be preferably used in a medical sustained-release carrier and an absorbent, a scaffolding for the regeneration medicine and the like.

Besides the above applications, the self-assembly is useful as: a stabilizer, a dispersant and a humectant in the food industry, agroforestry, cosmetics field and fiber industry; nano-parts in which metals or conductive materials are doped in the electronics and information field; and materials for a filter and conductive materials.

Then, the gel of the present invention can stably retain a gel structure over a wide range of liquid properties ranging from acidic to alkaline, particularly even under a neutral condition, so that the gel of the present invention is suitable for the applications of materials for the biochemistry such as a cell culture and of applications of medical materials.

In addition, the gel of the present invention can be obtained by adding the gelator in an amount smaller than that for the related-art gel as described above, so that the gel of the present invention is a gel having high safety both in the organism and in the environment.

Further, as described above, when the gel obtained from the long chain oxyaminopolyol which is a low molecular weight compound is used in an external environment, for example in the soil, the gel is easily degraded by soil bacteria or the like, or when the gel is used in an organism, the gel is easily degraded by metabolic enzyme, so that the gel applies low load to the environment and the organism.

BRIEF DESCRIPTION OF THE DRAWINGS

FIG. 1 is a schematic view showing a conceptual diagram of a self-assembly and a gelation following thereto of a gelator when the gelator is charged into an aqueous medium.

BEST MODES FOR CARRYING OUT THE INVENTION

Gelator

The gelator of the present invention contains a long chain oxyaminopolyol having a structure of the following Formula (I) or a pharmaceutically acceptable salt thereof and the long chain oxyaminopolyol is composed of a portion having a long chain with high lipophilicity which is derived from a higher alcohol, a portion derived from an amino acid and a portion derived from a polyol (gluconolactone).

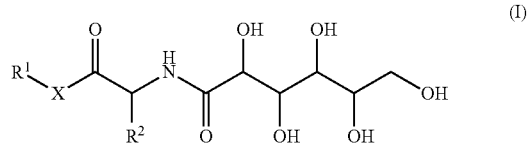

(I)

In the above Formula (1), $R^1$ contained in the portion derived from a higher alcohol is a $C_{12-16}$ saturated aliphatic group or a $C_{12-16}$ unsaturated aliphatic group having one double bond.

$R^1$ is preferably a $C_{14-16}$ saturated aliphatic group, particularly preferably a palmityl group.

$R^2$ is a hydrogen atom, a $C_{1-4}$ alkyl group which may have a $C_{1-2}$ branched chain, a phenylmethyl group or a —$(CH_2)_n$—Y group.

In the —$(CH_2)_n$—Y group, n is a number of 1 to 4, and Y is an amino group, a guanidino group, a —$CONH_2$ group or a fused heterocycle composed of a 5-membered ring, a 6-membered ring, or a 5-membered ring and a 6-membered ring which may have 1 to 3 nitrogen atom(s).

The $C_{1-4}$ alkyl group which may have a $C_{1-2}$ branched chain is preferably a methyl group, an ethyl group, an isopropyl group, an isobutyl group or a sec-butyl group, more preferably a methyl group, an isopropyl group, an isobutyl group or a sec-butyl group, most preferably a methyl group.

In the —$(CH_2)_n$—Y group, Y is preferably an amino group, a pyrrole group, an imidazole group, a pyrazole group or an indole group. Accordingly, the —$(CH_2)_n$—Y group is preferably a 2-aminoethyl group, a 4-aminobutyl group, a 4-amino-pyrrolemethyl group, an imidazolemethyl group, a pyrazolemethyl group or a 3-indolemethyl group.

Among them, $R^2$ is preferably a hydrogen atom, a methyl group, an isopropyl group, a sec-butyl group, an isobutyl group or a phenylmethyl group, particularly preferably an isopropyl group, a sec-butyl group, an isobutyl group or a phenylmethyl group.

X is an oxygen atom or a NH group, particularly preferably an oxygen atom.

[Self-Assembly Formed from Gelator]

When the gelator of the present invention is charged into water, an aqueous solution, a hydrophilic organic solvent or a hydrophilic organic solution, the portion derived from an amino acid or the portion derived from a polyol in Formula (I) form an intermolecular non-covalent bond through a hydrogen bond, and on the other hand, the portion derived from a higher alcohol in Formula (I) is self-assembled (or mentioned also as "self-organized") so as to be hydrophobically packed to form a self-assembly.

For reference, in FIG. 1, there is shown one example of the conceptual diagram of the self-assembly and gelation of the long chain oxyaminopolyol constituting the gelator of the present invention (with the proviso that in the present invention, all long chain oxyaminopolyols do not necessarily take a form of the self-assembly or gelation shown in FIG. 1).

Molecules of the long chain oxyaminopolyol (a) are assembled with a central focus on the portion derived from a higher alcohol which is a hydrophobic moiety (b) to form a self-assembly (c) by the self-assembly. Although the form of the self-assembly is not limited, examples thereof include a cylindrical form and a plate form.

Here, when the gelator of the present invention is charged into a hydrophobic organic solvent such as a vegetable oil or a hydrophobic organic solution, as opposed to the above mechanism, the portion derived from an amino acid and the portion derived from a polyol in Formula (I) is self-assembled so as to be hydrophilically packed to form a self-assembly.

[Gel]

When the self-assembly is formed in an aqueous medium such as water, an aqueous solution, a hydrophilic organic solvent and a hydrophilic organic solution, the self-assembly forms a three-dimensional network structure (for example, refer to (d) in FIG. 1) and further, a non-covalent bond is formed between the hydrophilic portion (portion derived from an amino acid, portion derived from a polyol) in the surface of the self-assembly and an aqueous medium, and the self-assembly swells, so that the aqueous medium is gelled to form a hydrogel.

In addition, when the self-assembly is formed in a hydrophobic medium such as a vegetable oil (hydrophobic organic solvent), the self-assembly forms a three-dimensional network structure in substantially the same manner and further, a hydrophobic portion (portion derived from a higher alcohol) in the surface of the self-assembly and a hydrophobic medium are assembled through a hydrophobic interaction, so that the hydrophobic medium is gelled to form a gel.

Although the aqueous medium is not particularly limited so long as it does not interrupt the self-assembly or gelation of the gelator, preferred specific examples of the aqueous medium available include water, an aqueous solution (called as "aqueous solution" in the present specification) in which an organic or inorganic acid or an organic or inorganic salt is dissolved in water, a hydrophilic organic solvent and a solvent mixture (called as "hydrophilic organic solution" in the present specification) of water and a hydrophilic organic solvent.

The hydrophilic organic solvent means an organic solvent that is dissolved in water at any ratio and examples thereof include alcohols, acetones, dioxanes and glycerins.

The alcohol is preferably a water-soluble alcohol that is freely dissolved in water and more preferred examples thereof include $C_{1-9}$ alcohols, polyhydric alcohols, higher alcohols and glycerides.

Specific examples of the $C_{1-9}$ alcohol, the polyhydric alcohol, the higher alcohol and the glycerides respectively include: methanol, ethanol, 2-propanol, isobutanol, pentanol, hexanol, 1-octanol and isooctanol as the $C_{1-9}$ alcohol; ethylene glycol, propylene glycol and polypropylene glycol as the polyhydric alcohol; octyldodecanol, stearyl alcohol and oleyl alcohol as the higher alcohol; and trioctanoin, glyceryl tri (caprylcaprylate) and glyceryl stearate as the glycerides.

The organic acid or the inorganic acid may be added in combination of two or more types thereof and preferred examples of the organic acid include acetic acid, citric acid, succinic acid, lactic acid, malic acid, maleic acid, fumaric acid and trifluoroacetic acid. More preferred examples thereof include acetic acid, citric acid, succinic acid, lactic acid and malic acid and further preferred examples thereof include acetic acid, citric acid and lactic acid.

In addition, preferred examples of the inorganic acid include hydrochloric acid, phosphoric acid, carbonic acid, sulfuric acid, nitric acid and boric acid. More preferred examples thereof include hydrochloric acid, phosphoric acid, carbonic acid and sulfuric acid and further preferred examples thereof include hydrochloric acid, phosphoric acid and carbonic acid.

The inorganic salt or the organic salt may be added in combination of two or more types thereof, however, preferably, the salt is added individually or in combination of two types thereof. By adding two types of salts, the solution has a buffer capacity, which is also desired.

Preferred examples of the inorganic salt include an inorganic carbonate salt, an inorganic sulfate salt, an inorganic phosphate salt and an inorganic hydrogen phosphate salt. More preferred examples thereof include calcium carbonate, sodium carbonate, potassium carbonate, sodium sulfate, potassium sulfate, magnesium sulfate, potassium phosphate, sodium phosphate, disodium hydrogen phosphate and sodium dihydrogen phosphate and further preferred examples thereof include calcium carbonate, magnesium sulfate, disodium hydrogen phosphate and sodium dihydrogen phosphate.

In addition, preferred examples of the organic salt include: inorganic salts of organic acids such as an inorganic acetate salt, an inorganic sulfate salt and an inorganic citrate salt; organic amine hydrochloride salts; and organic amine acetate salts. More preferred examples thereof include sodium acetate, potassium acetate, sodium lactate, potassium lactate, sodium citrate, potassium citrate, ethylenediamine hydrochloride salt, ethylenediamine tetraacetate salt and tris-hydroxymethylaminomethane hydrochloride salt.

Although the hydrophobic medium is not particularly limited so long as it does not interrupt the self-assembly or gelation of the gelling ability, preferred specific examples of the hydrophobic medium available include at least one of hydrophobic organic solvent selected from a group consisting of a vegetable oil, esters and hydrocarbons, and a solvent mixture (called as "hydrophobic organic solution" in the present specification) of the hydrophobic organic solvent and water.

Preferred specific examples of the hydrophobic organic solvent include: vegetable oils such as olive oil, coconut oil, caster oil, jojoba oil and sunflower oil; esters such as cetyl octanoate, isopropyl myristate and isopropyl palmitate; and hydro carbons such as toluene, xylene, n-hexane, cyclohexane, mineral oil and hydrogenated polyisobutene.

In addition, as the mechanism during the formation of the hydrogel when the gelator of the present invention is charged into an aqueous medium, the following mechanisms are considered.

That is, at a hydroxyl group moiety (portion derived from a polyol) of the long chain oxyaminopolyol constituting the gelator, a hydrogen atom is not dissociated under conditions ranging from acidic to neutral and a hydrogen bond between the hydroxyl groups is formed to perform the self-assembly. On the other hand, in an alkaline range, a hydrogen atom is dissociated and thereto, a metal ion existing in the solution is bonded, so that a crosslinkage can be formed through the metal ion to perform the self-assembly.

As described above, the gelator of the present invention can form a stable gel even in a neutral range. In addition, because the gelator of the present invention is a gelator containing a long chain oxyaminopolyol which is a low molecular weight compound produced using a nature-derived material or a material having safety as a raw material, both the gelator and the gel obtained therefrom are degradable in the environment and the organism, and thus a gelator and a gel having high biocompatibility can be obtained.

Therefore, the gelator and the gel obtained therefrom of the present invention can be used in materials for various fields such as cell culture base materials, preservation materials for organism molecules such as cells and proteins, base materials for external use, materials for medical use, materials for biochemistry, cosmetics materials, food materials, contact lenses, paper diapers, artificial actuators, and materials for dry-land agriculture. In addition, as a bioreactor carrier such as enzymes, the gelator and the gel obtained therefrom of the present invention can be widely utilized in studies, medicines, analyses and various industries.

Moreover, because the gel of the present invention is a gel formed from a low molecular weight compound (long chain oxyaminopolyol), by a setting of the compound, various functions, for example, capable of forming a gel performing a sol-gel conversion by responding to an external stimulation, can be easily imparted to the gel without a necessity of modifying a polymer chain or effecting a copolymerization reaction.

WORKING EXAMPLES

The present invention will be further described in more detail referring to working examples which should not be construed as limiting the scope of the present invention.

Example 1

Synthesis of Long Chain Oxyaminopolyol of Formula (1)

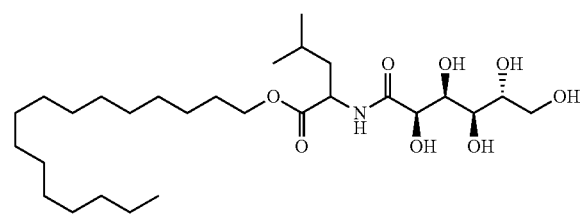

(1)

Palmityl alcohol (12.1 g, 50 mmol) and leucine (6.56 g, 50 mmol) were suspended in toluene (300 mL) and to the resultant suspension, p-toluenesulfonic acid monohydrate (11.4 g, 60 mmol) was added, followed by heating and refluxing the resultant mixture for 4 hours. The resultant reaction mixture was left to be cooled down and was concentrated to the half volume or less under reduced pressure. The concentrated reaction mixture was diluted with chloroform and the diluted reaction mixture was washed with a saturated sodium hydrogen carbonate aqueous solution.

The organic phase was dried over magnesium sulfate anhydride, filtered and concentrated under reduced pressure. The resultant residue was dispersed in acetone, and to the resultant dispersion, concentrated hydrochloric acid was added to form a precipitate, followed by sucking and filtering the dispersion using a Kiriyama funnel to produce a precipitate. The obtained precipitate was washed with acetone and then diluted with chloroform and the diluted precipitate was washed with a saturated sodium hydrogen carbonate aqueous solution. The organic phase was dried over magnesium sulfate anhydride, filtered and then concentrated under reduced pressure to produce a residue (14.2 g, 40 mmol).

The thus obtained residue was dissolved in ethanol (300 mL), and to the resultant solution, D-(+)-glucono-1,5-lactone (8.91 g, 50 mmol) was added, followed by heating and refluxing the resultant mixture for 5 hours. The resultant reaction mixture was left to be cooled down and then was concentrated under reduced pressure and the resultant crystal was dissolved in 1,4-dioxane. The resultant solution was filtered twice while heating the solution, and the resultant filtrate was concentrated under reduced pressure, followed by vacuum drying the concentrated filtrate to produce a long chain oxyaminopolyol (17.7 g, 33 mmol, yield: 66.2%) of Formula (1) as a white solid. NMR, IR and MS spectra data were measured with respect to the obtained long chain oxyaminopolyol.

$^1$H-NMR (500 MHz DMSO-d$_6$ δ ppm): 7.82 (d, J=8.0 Hz, 1H), 5.35 (d, J=5.4 Hz, 1H), 4.50 (d, J=5.0 Hz, 1H), 4.40 (d, J=5.5 Hz, 1H), 4.32 (m, 3H), 4.05 (m, 3H), 3.87 (m, 2H), 3.57 (m, 1H), 3.46 (m, 2H), 1.56 (m, 5H), 1.24 (m, 26H), 0.85 (m, 9H);

IR (nujol): 3396 cm$^{-1}$, 2918 cm$^{-1}$, 2850 cm$^{-1}$, 1736 cm$^{-1}$, 1657 cm$^{-1}$, 1531 cm$^{-1}$, 1469 cm$^{-1}$;

FT-MS$^+$ m/z calc. for C28H55O8N1 [M] +533.73820. found.

EST-MS$^+$ m/z calc. for C28H55NO8 [M] +533.39. found 534.40.

Working Example 1

Gelation Test (1)

To a solution selected from water, a 0.1 M HCl aqueous solution, ethanol, isooctanol and olive oil, the long chain oxyaminopolyol of Formula (1) obtained in the above Example 1 in an appropriate amount was added and the resultant mixture was warmed to 80° C. or more to dissolve the solid, followed by leaving the resultant solution to cool down. After cooled down, a state where the fluidity of the solution was lost and when the sample tube was inverted, the solution did not flow down, was evaluated as "gelled". The result is shown in Table 1.

TABLE 1

| Solvent | Gelator concentration |
|---|---|
| Water | 0.3% by weight |
| 0.1 M HCl aqueous solution | 0.6% by weight |
| Ethanol | 2.0% by weight |
| Isooctanol | 1.0% by weight or less |
| Olive oil | 1.0% by weight or less |

Example 2

Synthesis of Long Chain Oxyaminopolyol of Formula (2)

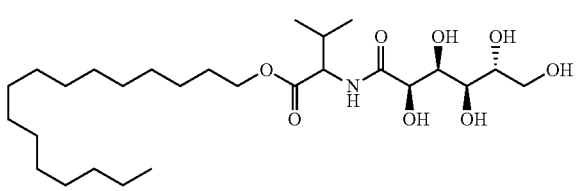

(2)

Palmityl alcohol (12.1 g, 50 mmol) and valine (5.86 g, 50 mmol) were suspended in toluene (300 mL), and to the resultant suspension, p-toluenesulfonic acid monohydrate (11.4 g, 60 mmol) was added, followed by heating and refluxing the resultant mixture for 4 hours. The resultant reaction mixture was left to be cooled down and then was concentrated to the half volume or less under reduced pressure. The concentrated reaction mixture was diluted with chloroform and the diluted reaction mixture was washed with a saturated sodium hydrogen carbonate aqueous solution.

The organic phase was dried over magnesium sulfate anhydride, filtered and concentrated under reduced pressure. The resultant residue was dispersed in acetone, and to the resultant dispersion, concentrated hydrochloric acid was added to form a precipitate, followed by sucking and filtering the dispersion using a Kiriyama funnel to produce a precipitate. The obtained precipitate was washed with acetone and then diluted with chloroform and the diluted precipitate was washed with a saturated sodium hydrogen carbonate aqueous solution. The organic phase was dried over magnesium sulfate anhydride, filtered and then concentrated under reduced pressure to produce a residue (11.65 g, 34 mmol).

The thus obtained residue was dissolved in ethanol (200 mL) and to the resultant solution, D-(+)-glucono-1,5-lactone (7.13 g, 40 mmol) was added, followed by heating and refluxing the resultant mixture for 5 hours. The resultant reaction mixture was left to be cooled down and then was concentrated under reduced pressure and the resultant crystal was dissolved in 1,4-dioxane. The resultant solution was filtered twice while heating the solution, and the resultant filtrate was concentrated under reduced pressure, followed by vacuum drying the concentrated filtrate to produce a long chain oxyaminopolyol (15.6 g, 30 mmol, yield: 60.0%) of Formula (2) as a white solid. NMR, IR and MS spectra data were measured with respect to the obtained long chain oxyaminopolyol.

$^1$H-NMR (500 MHz DMSO-$d_6$ δ ppm): 7.60 (d, J=8.7 Hz, 1H), 5.46 (d, J=5.4 Hz, 1H), 4.53 (d, J=4.7 Hz, 1H), 4.44 (d, J=5.1 Hz, 1H), 4.38 (d, J=7.0 Hz, 1H), 4.33 (t, J=5.6 Hz, 3H), 4.23 (m, 1H), 4.09 (m, 2H), 4.04 (m, 1H), 3.89 (m, 2H), 3.57 (m, 1H), 3.48 (m, 1H), 2.05 (m, 1H), 1.57 (m, 2H), 1.24 (m, 26H), 0.86 (m, 9H);

IR (nujol): 3400 cm$^{-1}$, 3350 cm$^{-1}$, 2981 cm$^{-1}$, 2851 cm$^{-1}$, 1735 cm$^{-1}$, 1659 cm$^{-1}$, 1533 cm$^{-1}$, 1266 cm$^{-1}$;

FT-MS$^+$ m/z calc. for C27H53O8N1 [M] +519.71162. found.

EST-MS$^+$ m/z calc. for C27H53NO8 [M] +519.38. found 520.38.

Working Example 2

Gelation Test (2)

To a solution selected from water, a 0.1 M HCl aqueous solution, a pH 3 aqueous solution, a pH 5 aqueous solution, a pH 7 aqueous solution, a pH 8 aqueous solution, isooctanol, toluene and olive oil, the long chain oxyaminopolyol of Formula (2) obtained in the above Example 2 in an appropriate amount was added, and the resultant mixture was warmed to 80° C. or more to dissolve the solid, followed by leaving the resultant solution to cool down. After cooled down, a state where the fluidity of the solution was lost and when the sample tube was inverted, the solution did not flow down, was evaluated as "gelled". The result is shown in Table 2.

TABLE 2

| Solvent | Gelator concentration |
| --- | --- |
| Water | 0.3% by weight |
| 0.1 M HCl aqueous solution | 0.2% by weight |
| Any of aqueous solutions of pH 3, 5, 7 and 8 | 0.5% by weight |
| Isooctanol | 1.0% by weight or less |
| Toluene | 1.0% by weight or less |
| Olive oil | 1.0% by weight or less |

Example 3

Synthesis of Long Chain Oxyaminopolyol of Formula (3)

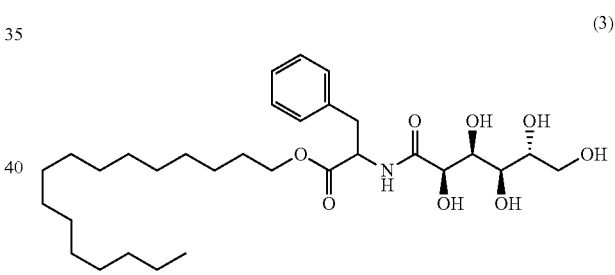

(3)

Palmityl alcohol (12.1 g, 50 mmol) and L-phenylalanine (8.26 g, 50 mmol) were suspended in toluene (300 mL), and to the resultant suspension, p-toluenesulfonic acid monohydrate (11.4 g, 60 mmol) was added, followed by heating and refluxing the resultant mixture for 4 hours. The resultant reaction mixture was left to be cooled down and then concentrated to the half volume or less under reduced pressure. The concentrated reaction mixture was diluted with chloroform and the diluted reaction mixture was washed with a saturated sodium hydrogen carbonate aqueous solution.

The organic phase was dried over magnesium sulfate anhydride, filtered and concentrated under reduced pressure. The resultant residue was dispersed in acetone, and to the resultant dispersion, concentrated hydrochloric acid was added to form a precipitate, followed by sucking and filtering the dispersion using a Kiriyama funnel to produce a precipitate. The obtained precipitate was washed with acetone and then diluted with chloroform, and the diluted precipitate was washed with a saturated sodium hydrogen carbonate aqueous solution. The organic phase was dried over magnesium sulfate anhydride, filtered and then concentrated under reduced pressure to produce a residue (15.2 g, 39 mmol).

The thus obtained residue was dissolved in ethanol (200 mL), and to the resultant solution, D-(+)-glucono-1,5-lactone (8.91 g, 50 mmol) was added, followed by heating and refluxing the resultant mixture for 5 hours. The resultant reaction mixture was left to be cooled down and was then concentrated under reduced pressure, and the resultant crystal was dissolved in 1,4-dioxane. The resultant solution was filtered twice while heating the solution, and the resultant filtrate was concentrated under reduced pressure, followed by vacuum drying the concentrated filtrate to produce a long chain oxyaminopolyol (18.54 g, 33 mmol, yield: 66.0%) of Formula (3) as a white solid. NMR, IR and MS spectra data were measured with respect to the obtained long chain oxyaminopolyol.

$^1$H-NMR (500 MHz DMSO-$d_6$ δ ppm): 7.79 (d, J=7.8 Hz, 1H), 7.27 (m, J=7.4 Hz, 2H), 7.18 (m, 3H), 5.43 (d, J=5.2 Hz, 1H), 4.54 (m, 2H), 4.44 (d, J=5.3 Hz, 1H), 4.34 (m, 2H), 3.98 (m, 1H), 3.89 (m, 1H), 3.57 (m, H), 3.47 (m, 2H), 3.04 (d, J=6.7 Hz, 2H), 1.48 (m, 2H), 1.24 (m, 26H), 0.85 (t, 3H);

IR (nujol): 3289 cm$^{-1}$, 2918 cm$^{-1}$, 2850 cm$^{-1}$, 1744 cm$^{-1}$, 1651 cm$^{-1}$, 1529 cm$^{-1}$, 1360 cm$^{-1}$;

FT-MS$^+$ m/z calc. for C31H53O8N1 [M] +567.75442. found.

EST-MS$^+$ m/z calc. for C31H53NO8 [M] +567.38. found 568.38.

Working Example 3

Gelation Test (3)

To a solution selected from water, isooctanol and toluene, the long chain oxyaminopolyol of Formula (3) obtained in the above Example 3 in an appropriate amount was added, and the resultant mixture was warmed to 80° C. or more to dissolve the solid, followed by leaving the resultant solution to cool down. After cooled down, a state where the fluidity of the solution was lost, and when the sample tube was inverted, the solution did not flow down, was evaluated as "gelled". The result is shown in Table 3.

TABLE 3

| Solvent | Gelator concentration |
| --- | --- |
| Water | 0.3% by weight |
| Isooctanol | 1.0% by weight or less |
| Toluene | 1.0% by weight or less |

Example 4

Synthesis of Long Chain Oxyaminopolyol of Formula (4)

(4)

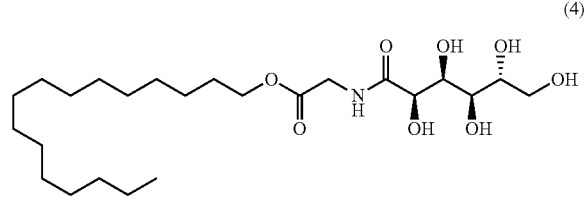 [SMILES: CCCCCCCCCCCCCCCCOC(=O)CNC(=O)[C@H](O)[C@@H](O)[C@H](O)[C@H](O)CO]

Palmityl alcohol (41.1 g, 170 mmol) and glycine (12.8 g, 170 mmol) were suspended in toluene (500 mL), and to the resultant suspension, p-toluenesulfonic acid monohydrate (40.25 g, 212 mmol) was added, followed by heating and refluxing the resultant mixture for 4 hours. The resultant reaction mixture was left to be cooled down and then was concentrated to the half volume or less under reduced pressure. The concentrated reaction mixture was diluted with methylene chloride, and the diluted reaction mixture was washed with a saturated sodium hydrogen carbonate aqueous solution and a saturated saline in this order.

The organic phase was dried over magnesium sulfate anhydride, filtered and concentrated under reduced pressure. The resultant residue was dispersed in acetone, and to the resultant dispersion, concentrated hydrochloric acid was added to form a precipitate, followed by sucking and filtering the dispersion using a Kiriyama funnel to produce a precipitate. The obtained precipitate was washed with acetone and diluted with chloroform, and the diluted precipitate was washed with a saturated sodium hydrogen carbonate aqueous solution. The organic phase was dried over magnesium sulfate anhydride, filtered and then concentrated under reduced pressure.

The thus obtained compound (48.0 g, 158 mmol) was dissolved in ethanol (750 mL), and to the resultant solution, D-(+)-glucono-1,5-lactone (31.04 g, 174 mmol) was added, followed by heating and refluxing the resultant mixture for 5 hours. The resultant reaction mixture was left to be cooled down and then was concentrated under reduced pressure, and the resultant crystal was dissolved in 1,4-dioxane. The resultant solution was filtered twice while heating the solution, and the resultant filtrate was concentrated under reduced pressure, followed by vacuum drying the concentrated filtrate to produce a long chain oxyaminopolyol (35.00 g, 76.6 mmol, yield: 45.0%) of Formula (4) as a white solid. NMR, IR and MS spectra data were measured with respect to the obtained long chain oxyaminopolyol.

$^1$H-NMR (500 MHz DMSO-$d_6$ δ ppm): 8.00 (t, J=6.0 Hz, 1H), 5.49 (d, J=4.9 Hz, 1H), 4.54 (d, J=5.0 Hz, 1H), 4.47 (d, J=5.5 Hz, 1H), 4.36 (t, J=7.1 Hz, 1H), 4.34 (t, J=5.7 Hz, 1H), 4.03 (m, 3H), 3.90 (m, 2H), 3.79 (m, 1H), 3.57 (m, 1H), 3.49 (m, 2H), 1.56 (m, 2H), 1.24 (m, 26H), 0.86 (t, J=6.9 Hz, 3H);

IR (nujol): 3511 cm$^{-1}$, 2918 cm$^{-1}$, 2849 cm$^{-1}$, 1726 cm$^{-1}$, 1635 cm$^{-1}$, 1362 cm$^{-1}$, 1239 cm$^{-1}$;

FT-MS$^+$ m/z calc. for C24H47O8N1 [M] +477.63188. found.

EST-MS$^+$ m/z calc. for C24H47NO8 [M] +477.33. found 478.34.

Working Example 4

Gelation Test (4)

To a solution selected from water, a 0.1 M HCl aqueous solution, isooctanol and toluene, the long chain oxyaminopolyol of Formula (4) obtained in the above Example 4 in an appropriate amount was added, and the resultant mixture was warmed to 80° C. or more to dissolve the solid, followed by leaving the resultant solution to cool down. After cooled down, a state where the fluidity of the solution was lost and when the sample tube was inverted, the solution did not flow down, was evaluated as "gelled". The result is shown in Table 4.

TABLE 4

| Solvent | Gelator concentration |
| --- | --- |
| Water | 0.8% by weight |
| 0.1 M HCl aqueous solution | 0.5% by weight |

TABLE 4-continued

| Solvent | Gelator concentration |
| --- | --- |
| Isooctanol | 1.0% by weight or less |
| Toluene | 2.1% by weight or less |

INDUSTRIAL APPLICABILITY

The gelator and the gel obtained therefrom according to the present invention can stably retain a gel structure over a wide range of liquid properties ranging from acidic to alkaline, particularly even under a neutral condition, and have extremely high biocompatibility, so that the gelator and the gel are suitable for the applications as various functional materials.

For example, from the viewpoint of suitability for the above wide range of liquid properties, the gelator and the gel are suitable for the applications such as cleaning agents (for medicine, living, industry and the like), sol-gelling agents (cosmetics and other commodities applications), a gelator for a dye stabilizing application, and food additives (for acidic food, alkaline food, neutral food, and the like), and the like.

In addition, the gelator and the gel can be applied in a neutral range, as materials for biology and biochemistry such as cell culture base materials and skin base materials, and in an acidic range, as base materials of pharmaceutical preparations such as gastric acid adjusters, enteric coated preparations and biodegradable anti-metabolic agents by the feeling of fullness, as stabilizers and additives during the production of acidic milk beverages containing pectin, etc., or in applications for improving an alkaline soil, or the like.

Further, in an alkaline range, the gelator and the gel can be used as stabilizers and additives during the production of alkaline beverages and milk beverages, as applications for catalytic reactions using various alkaline enzymes (alkaline protease, alkaline cerase, alkaline amylase, alkaline xylase, alkaline pectate lyase and the like), in industrial applications of alkalophilic bacteria, as gelators used in alkaline cells and the like, as acidic soil ameliorant applications, as base materials, reaction additives and accelerators in various industrial applications such as bioreactors, cleaning agents and soaps, cosmetics, drug discoveries, and analytic investigations.

The invention claimed is:

1. A gelator comprising a long chain oxyaminopolyol of Formula (I):

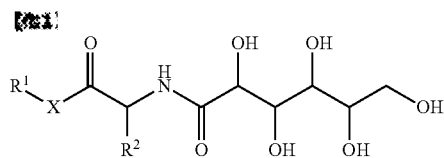

where $R^1$ is a $C_{12-16}$ saturated aliphatic group or a $C_{12-16}$ unsaturated aliphatic group having one double bond; $R^2$ is a phenylmethyl group; and X is an oxygen atom or a NH group, or a pharmaceutically available salt of the long chain oxyaminopolyol.

2. The gelator according to claim 1, wherein $R^1$ is a $C_{14-16}$ saturated aliphatic group.

3. The gelator according to claim 2, wherein $R^1$ is a palmityl group.

4. A self-assembly formed by self-assembly of the gelator according to claim 1.

5. A self-assembly formed by self-assembly of the gelator according to claim 2.

6. A self-assembly formed by self-assembly of the gelator according to claim 3.

* * * * *